(12) United States Patent
Hong et al.

(10) Patent No.: US 11,574,720 B2
(45) Date of Patent: Feb. 7, 2023

(54) SYSTEM AND METHOD FOR TRANSMITTING ELECTRONIC PRESCRIPTION ON THE BASIS OF CLOUD COMPUTING

(71) Applicant: LEMON HEALTHCARE LTD, Seoul (KR)

(72) Inventors: Byung Jin Hong, Seoul (KR); Kyung Hi Seo, Seoul (KR)

(73) Assignee: LEMON HEALTHCARE LTD, Seoul (KR)

( * ) Notice: Subject to any disclaimer, the term of this patent is extended or adjusted under 35 U.S.C. 154(b) by 373 days.

(21) Appl. No.: 16/632,023

(22) PCT Filed: May 17, 2019

(86) PCT No.: PCT/KR2019/005955
§ 371 (c)(1),
(2) Date: Jan. 17, 2020

(87) PCT Pub. No.: WO2020/105823
PCT Pub. Date: May 28, 2020

(65) Prior Publication Data
US 2021/0225473 A1    Jul. 22, 2021

(30) Foreign Application Priority Data
Nov. 23, 2018  (KR) .......................... 10-2018-0146440

(51) Int. Cl.
*G16H 20/10*    (2018.01)
*G16H 40/67*    (2018.01)
(Continued)

(52) U.S. Cl.
CPC ............. *G16H 20/10* (2018.01); *G06F 21/36* (2013.01); *G06F 21/6245* (2013.01);
(Continued)

(58) Field of Classification Search
CPC ........ G16H 20/10; G16H 40/67; G16H 10/60; G06F 21/36; G06F 21/6245; G06F 21/64
See application file for complete search history.

(56) References Cited

U.S. PATENT DOCUMENTS

| 2007/0192328 A1* | 8/2007 | Handa ................. G06F 16/2471 |
| 2014/0244309 A1* | 8/2014 | Francois ................ G16H 50/20 |
| | | 705/2 |

FOREIGN PATENT DOCUMENTS

| KR | 10-2012-0076666 A |   | 7/2012 |  |
| KR |    20120076666    | * | 7/2012 | ............. G06Q 50/22 |

(Continued)

OTHER PUBLICATIONS

International Search Report with partial English translation and Written Opinion dated Sep. 30, 2019 in corresponding International Application No. PCT/KR2019/005955; 9 pages.

*Primary Examiner* — Michael Tomaszewski
*Assistant Examiner* — Mohmad Muqueeth
(74) *Attorney, Agent, or Firm* — Novick, Kim & Lee PLLC; Byungwoong Park

(57) ABSTRACT

A system and a method for transmitting an electronic prescription on the basis of cloud computing. The cloud-based electronic prescription transmission method includes the steps of: requesting an electronic prescription from a hospital server, when a cloud server receives a request for the electronic prescription, by the cloud server; extracting patient information and prescription information stored in an EMR DB, by the hospital server; converting the prescription information according to a unique API, by an API builder unit; and authenticating the converted prescription information through an electronic signature of the clinic, encrypting the converted prescription information, and transmitting the electronic prescription to the cloud server, by the hospital server.

8 Claims, 4 Drawing Sheets

(51) Int. Cl.
*G16H 10/60* (2018.01)
*G06F 21/36* (2013.01)
*G06F 21/62* (2013.01)
*G06F 21/64* (2013.01)

(52) U.S. Cl.
CPC ............ *G06F 21/64* (2013.01); *G16H 10/60* (2018.01); *G16H 40/67* (2018.01)

(56) References Cited

FOREIGN PATENT DOCUMENTS

| KR | 10-1602778 B1 | 3/2016 |
| KR | 10-2017-0127587 A | 11/2017 |
| KR | 10-2018-0047226 A | 5/2018 |

* cited by examiner

SYSTEM AND METHOD FOR TRANSMITTING ELECTRONIC PRESCRIPTION ON THE BASIS OF CLOUD COMPUTING

TECHNICAL FIELD

The present invention relates to a system and a method for transmitting an electronic prescription on the basis of cloud computing, and more specifically, to a system and a method for transmitting an electronic prescription on the basis of cloud computing, in which a user can be provided with an electronic prescription in a cloud computing environment, and the user himself or herself may select a drugstore on an application and transmit the prescription to the drugstore.

BACKGROUND ART

Since the responsibility for a problem caused by identification of a prescribed medicine recorded by a doctor or a problem caused by a prescription or preparation error is unclear when a user himself or herself visits a drugstore and submits a paper prescription and this is inconvenient and troublesome from the standpoint of a patient, electronic prescription services are proposed recently.

Meanwhile, conventional electronic prescription services are still inconvenient in various aspects since when an electronic prescription for patient's keeping is transmitted from a hospital to a user terminal, the user himself or herself visits a drugstore and receives the prescribed medicine by showing the user terminal or using a QR code. In addition, although it is required to adopt cloud technologies as a solution of closed systems and poor information security of hospital, the cases of applying the cloud technologies are insufficient.

Although there is Korean Patent Registration No. 10-1329003 (Method, patient's client device and relay device for delivery each electronic prescription services of patient and pharmacy) as an prior patent thereof, it merely discloses a technique of creating unique information and transmitting an electronic prescription to a cellular phone terminal of a patient.

DISCLOSURE OF INVENTION

Technical Problem

Therefore, the present invention has been made in view of the above problems, and it is an object of the present invention to provide a system and a method for transmitting an electronic prescription on the basis of cloud computing, which can create an electronic prescription through a standardized API regardless of a DBMS of a hospital server or a type of development language, and provide the electronic prescription in a cloud computing environment.

Technical Solution

To accomplish the above object, according to one aspect of the present invention, there is provided a cloud-based electronic prescription transmission method comprising the steps of: requesting an electronic prescription from a hospital server, when a cloud server receives a request for the electronic prescription, by the cloud server; extracting patient information and prescription information stored in an EMR DB, by the hospital server; converting the prescription information according to a unique API, by an API builder unit; and authenticating the converted prescription information through an electronic signature of the clinic, encrypting the converted prescription information, and transmitting the electronic prescription to the cloud server, by the hospital server.

According to another aspect of the present invention, there is provided a cloud-based electronic prescription transmission system comprising: a cloud server for requesting an electronic prescription from a hospital server when a request for the electronic prescription is received from a user terminal, transmitting at least one among a created QR code, information on a drugstore selected by the user terminal, and the electronic prescription to a drugstore server when the electronic prescription is received from the hospital server, and deleting the electronic prescription when reception of a medicine is informed from the user terminal; the hospital server for extracting patient information and prescription information from an EMR DB unit when a request for the electronic prescription is received from the cloud server, converting the prescription information using a unique API through an API builder unit, authenticating the converted prescription information through an electronic signature of the clinic, encrypting the prescription information, and transmitting the electronic prescription to the cloud server; and the drugstore server for confirming the electronic prescription when at least one among the QR code, the electronic prescription, and the drugstore information is received from the cloud server, determining whether or not to prepare the medicine, calculating a medicine price, requesting the cloud server to make a payment, and storing the electronic prescription when completion of receiving the medicine is informed.

Advantageous Effects

According to the present invention, an electronic prescription can be created through a standardized API regardless of a heterogeneous DBMS of a hospital server or a type of development language.

In addition, according to the present invention, as a user may receive a prescription using a user terminal and submit the prescription to a drugstore, the waiting time for receiving the prescription, the time required for preparing a medicine, the waiting time for receiving the medicine can be reduced, and thus it is very convenient for the user. Furthermore, the user may inquire the prescription and make a payment for the medicine through a mobile terminal.

BEST MODE FOR CARRYING OUT THE INVENTION

Figure 1:
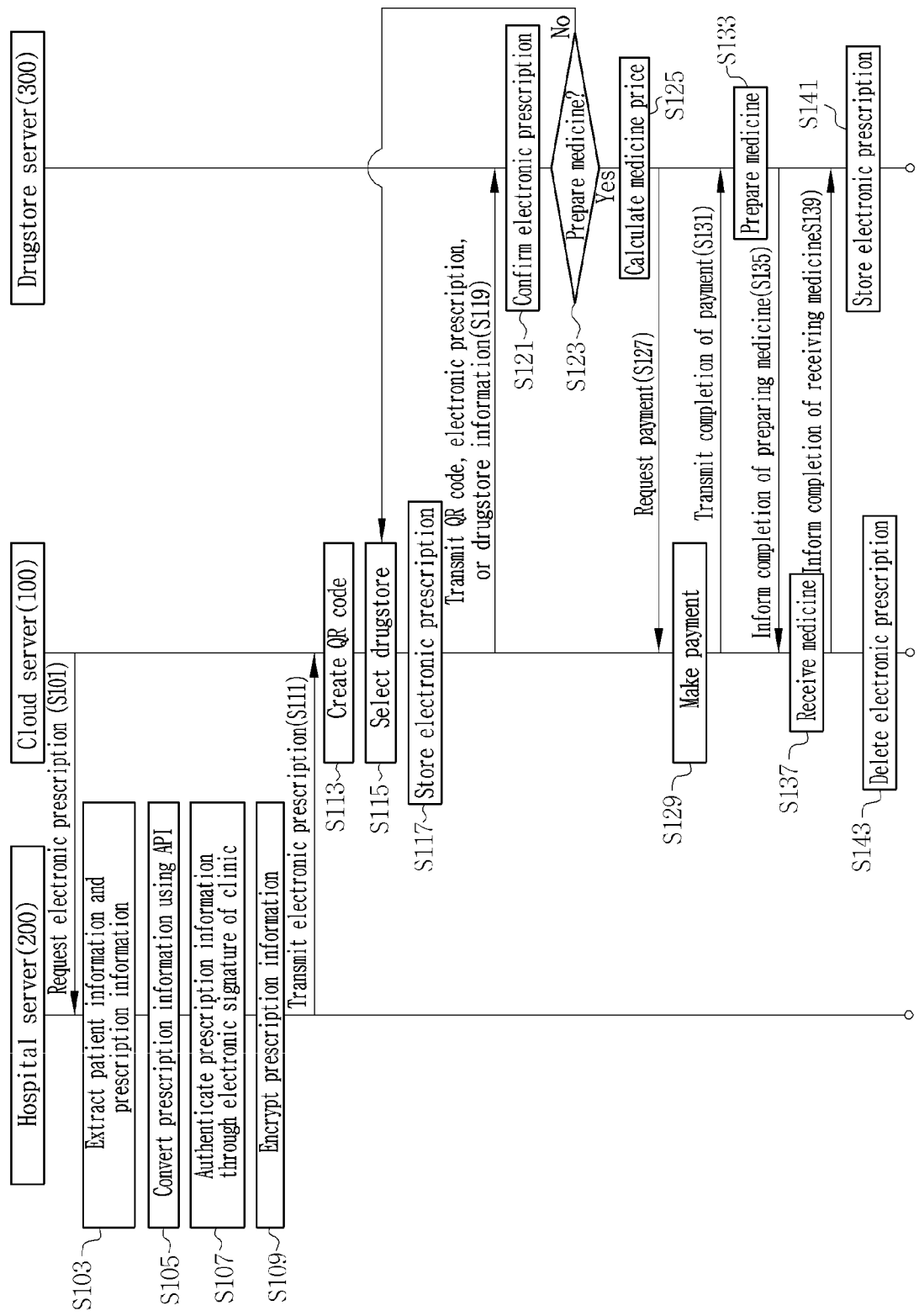
FIG. 1 is a sequence diagram illustrating a cloud-based electronic prescription transmission method according to an embodiment of the present invention.

Specific structural or functional description with respect to the embodiments according to the concept of the present invention disclosed in this specification is merely exemplified for the purpose of describing the embodiments according to the concept of the present invention, and the embodiments according to the concept of the present invention may be embodied in a variety of forms and are not limited to the embodiments described in this specification.

As the embodiments according to the concept of the present invention allows diverse changes and may have various forms, the embodiments will be illustrated in the drawings and described in detail in this specification. However, this is not intended to limit the embodiments according to the concept of the present invention to specific disclosed forms, and it is to be appreciated that all changes, equivalents, and substitutes that do not depart from the spirit and technical scope of the present invention are encompassed in the present invention.

The terms used herein are used only to describe particular embodiments and are not intended to limit the present invention. Singular expressions include plural expressions, unless the context clearly indicates otherwise. It will be further understood that the terms "include", "have" and the like used herein is to specify the presence of stated features, integers, steps, operations, elements, and/or components, but do not preclude in advance the presence or addition of one or more other features, integers, steps, operations, elements, components, and/or groups thereof.

Hereinafter, the embodiments of the present invention will be described in detail with reference to the accompanying drawings.

FIG. 1 is a sequence diagram illustrating a cloud-based electronic prescription transmission method according to an embodiment of the present invention.

Referring to FIG. 1, in a cloud-based electronic prescription transmission method, a cloud server 100 requests an electronic prescription from a hospital server 200 when a request for the electronic prescription is received from a user terminal 400 (step S101).

The hospital server 200 extracts patient information and prescription information stored in an EMR DB unit 210 (step S103), and an API builder unit 220 converts the prescription information according to an application programming interface (API) (step S105). At this point, the API is a standardized API which can convert the prescription information into standardized prescription information regardless of a heterogeneous database management system (DBMS) or a type of development language. The API builder unit 220 may create, manage and test an API for standardizing database information stored in the hospital server, such as the prescription information or the like. Although the API builder unit 220 may be installed and operate in the hospital server, it is not limited thereto. The API builder unit 220 converts the prescription information by extracting the prescription information from the EMR DB unit, creating a data source, creating an SQL query, and repeatedly performing test.

The hospital server 200 authenticates the converted prescription information through the electronic signature of the clinic (step S107) and encrypts the converted prescription information (step S109). The hospital server 200 transmits an electronic prescription to the cloud server 100 (step S111). The electronic prescription includes the converted prescription information and the patient information.

The cloud server 100 creates a QR code (step S113), and when a drugstore is selected by the user terminal 400, the cloud server 100 temporarily stores the electronic prescription (step S117). At this point, the QR code may be replaced by a hash code which provides location information of the prescription information. The cloud server 100 transmits at least one among the QR code, the electronic prescription, and drugstore information on the selected drugstore to a drugstore server 300 (step S119).

The drugstore server 300 confirms the electronic prescription (step S121), determines whether or not to prepare the medicine (step S123), and calculates a medicine price when preparation of the medicine is performed (step S125).

The drugstore server 300 requests the cloud server 100 to make a payment (step S127), and when making the payment is completed by the user terminal 400, the cloud server 100 transmits completion of payment to the drugstore server 300 (step S131).

The drugstore server 300 prepares the medicine (step S133) and informs the cloud server 100 of completion of preparing the medicine when preparation of the medicine is completed (step S135), and when the cloud server 100 informs the drugstore server 300 of completion of receiving the medicine (step S139), the drugstore server 300 stores the electronic prescription, and the cloud server 100 deletes the electronic prescription (step S143).

That is, in the present invention, prescription information may be transferred and used online through a cloud server at any time at any place, and as the electronic prescription is deleted from the cloud server when preparation of the medicine is completed, security of the system is enhanced. In addition, the time for receiving a prescription at a hospital, the time for preparing a medicine at a drugstore, and the waiting time for receiving the medicine can be reduced, and furthermore, it is possible to make a payment for the medicine, and user's convenience can be enhanced.

Figure 2:
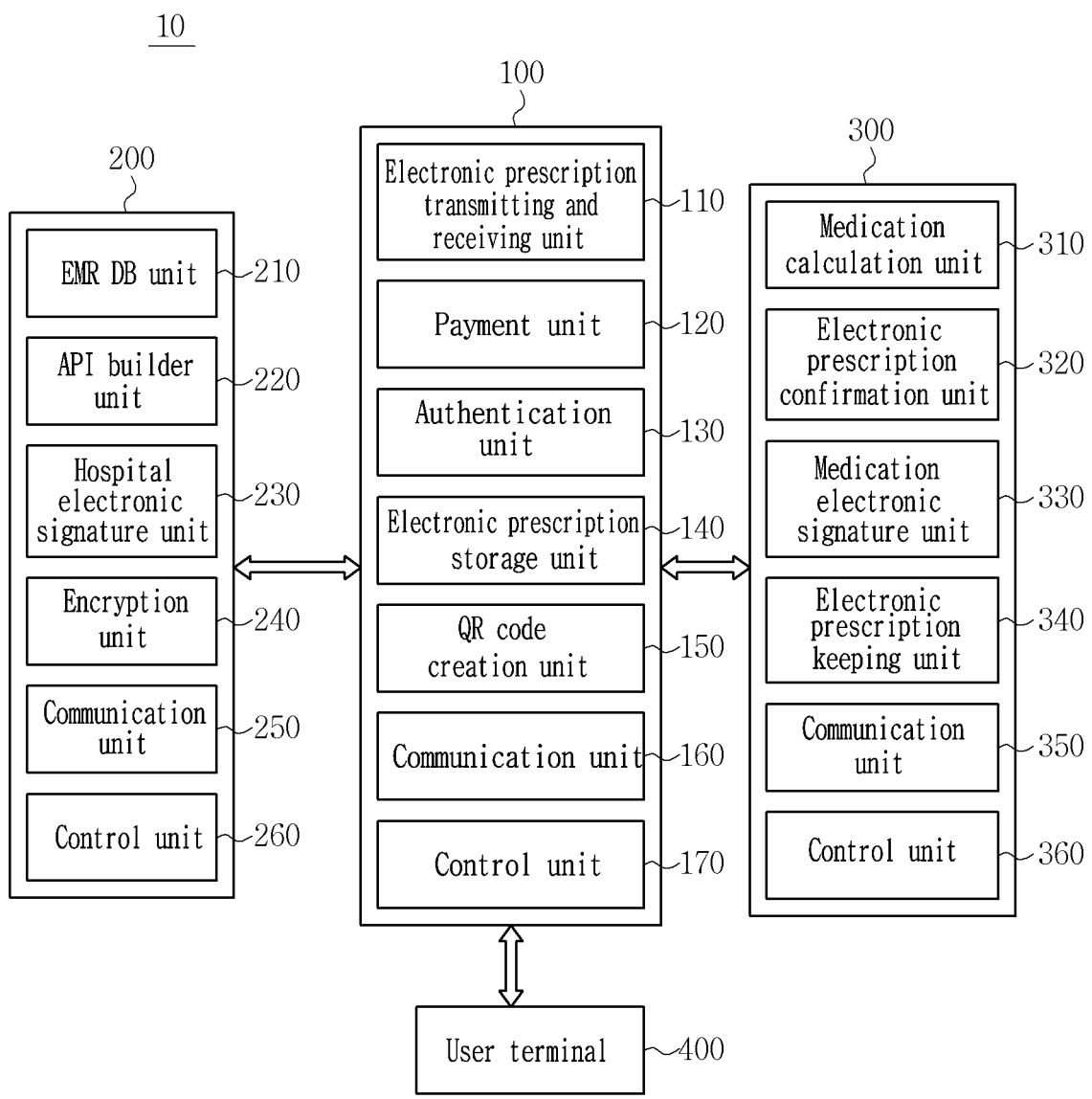
FIG. 2 is a view showing the configuration of an electronic prescription transmission system according to an embodiment of the present invention.

FIG. 2 is a view showing the configuration of an electronic prescription transmission system according to an embodiment of the present invention.

Referring to FIG. 2, an electronic prescription transmission system 10 is configured of a cloud server 100, a hospital server 200, a drugstore server 300, and a user terminal 400. When the user terminal 400 requests an electronic prescription, the cloud server 100 requests the electronic prescription from the hospital server 200, and the hospital server 200 converts and encrypts prescription information using a standardized API and provides the cloud server 100 with the electronic prescription. The cloud server 100 transfers the electronic prescription to the drugstore server 300, and functions of preparing a medicine and making a payment are performed.

The cloud server 100 includes an electronic prescription transmitting and receiving unit 110, a payment unit 120, an authentication unit 130, an electronic prescription storage unit 140, a QR code creation unit 150, a communication unit 160, and a control unit 170.

When the user terminal 400 requests an electronic prescription, the electronic prescription transmitting and receiving unit 110 may request the electronic prescription from the hospital server 200. In addition, when the electronic prescription is received from the hospital server 200, the electronic prescription transmitting and receiving unit 110 may transfer the electronic prescription to the drugstore server 300. When a request for making a payment for the medicine is received from the drugstore server 300, the payment unit 120 may provide the user terminal with a payment service. When making the payment is completed, the payment unit 120 may transmit payment completion to the drugstore server 300. The authentication unit 130 may perform authentication by comparing personal information received from the user terminal 400 and patient information received from the hospital server. The electronic prescription storage unit 140 may enhance security by temporarily storing the electronic prescription when the electronic prescription is received from the hospital server 200 and deleting the stored electronic prescription when reception of the medicine is informed from the user terminal. The QR code creation unit 150 may create a QR code corresponding to the received electronic prescription and transmit the QR code to the drugstore server 300. At this point, the QR code creation unit 150 may create and provide a hash code which provides location information of the prescription information. The communication unit 160 may communicate with the hospital server 200, the drugstore server 300 and the user terminal 400 using a wired or wireless network. The control unit 170 may control each configuration of the cloud server.

The hospital server 200 includes an EMR DB unit 210, an API builder unit 220, a hospital electronic signature unit 230, an encryption unit 240, a communication unit 250, and a control unit 260.

The EMR DB unit 210 may store patient information, medical treatment information, prescription information, clinic administration information, and history information. The types of the information stored in the EMR DB unit 210 are not limited.

The API builder unit 220 extracts patient information and prescription information from the EMR DB unit 210 and converts the patient information and the prescription information using an API. That is, the API builder unit may converts the prescription information by creating a data source, conveniently creating an SQL query through an SQL query creation guide, converting the data source into a standard data through an API builder, and repeatedly verifying the data. Therefore, data of heterogeneous DBMSs and data developed in different development languages can be standardized through the process.

The hospital electronic signature unit 230 performs authentication on the converted prescription information through the electronic signature of the clinic. The encryption unit 240 may enhance security of the converted prescription information by means of encryption, and the communication unit 250 may transmit and receive data to and from the cloud server 100, and the control unit 260 may control each configuration of the hospital server.

The drugstore server 300 includes a medication calculation unit 310, an electronic prescription confirmation unit 320, a medication electronic signature unit 330, an electronic prescription keeping unit 340, a communication unit 350, and a control unit 360.

The medication calculation unit 310 may calculate a medicine price on the basis of the prescription information and request payment of the medicine price from the cloud server 100. The electronic prescription confirmation unit 320 may confirm the received electronic prescription and determine whether or not to prepare the medicine. The medication electronic signature unit 330 may put an electronic signature of the clinic on an electronic prescription for drugstore's keeping and store the electronic prescription in the electronic prescription keeping unit 340. The communication unit 350 may transmit and receive data to and from the cloud server 100, and the control unit 360 may control each configuration of the drugstore server.

Figure 3:
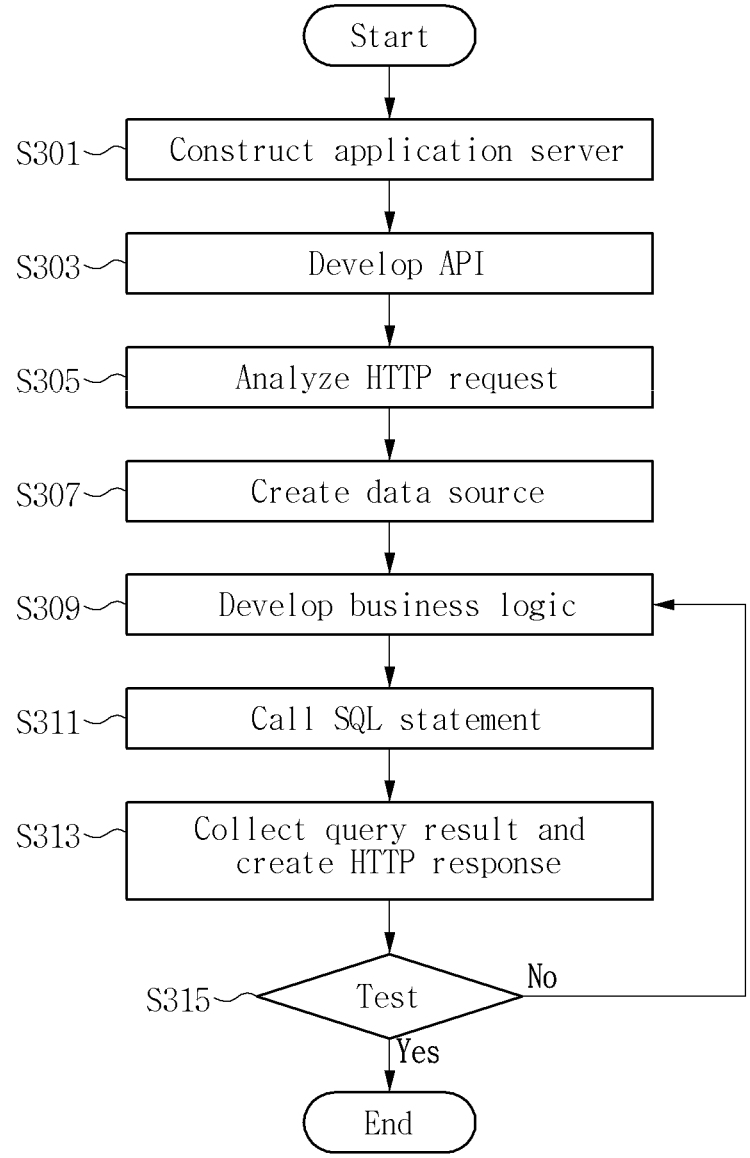
FIGS. 3 and 4 are flowcharts illustrating an operation method of an API builder unit according to an embodiment of the present invention.
Figure 4:
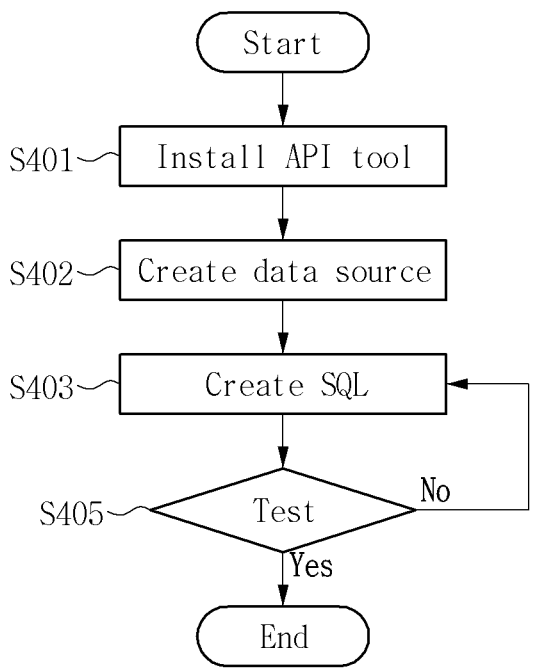

FIGS. 3 and 4 are flowcharts illustrating an operation method of an API builder unit according to an embodiment of the present invention.

Referring to FIGS. 3 and 4, the API builder unit constructs an application server (step S301). The API builder unit develops an API (step S303) and analyzes an HTTP request (step S305). At this point, although the application server may be constructed as IIS, Tomcat Tuxedo, Entra or the like, it is not limited thereto. The API is a REST API and may be implemented in a language such as .Net ASP, Java or C.

Then, the API builder unit receives information from the EMR DB and creates a data source (step S307) and develops business logic (step S309). Then, the API builder unit calls an SQL statement, collects query results, and creates an HTTP response (step S313). The process terminates when a criterion is satisfied through a test or returns to the business logic development step when the criterion is not satisfied.

In addition, in another embodiment, the API builder unit installs an API tool (step S401) and creates a data source (step S403). Then, the API builder unit creates an SQL query (step S405) and repeats a test (step S407).

Figure 5:
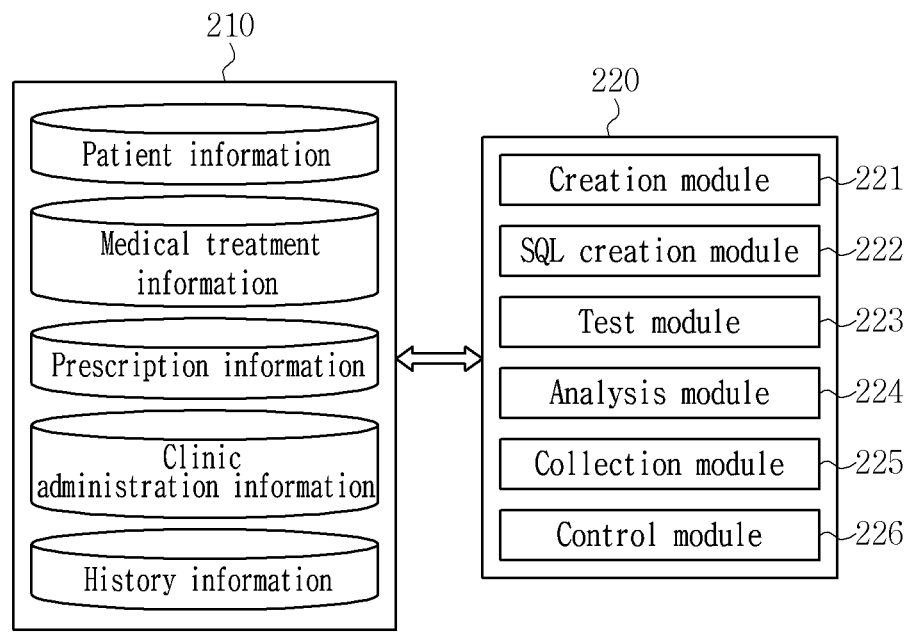
FIG. 5 is a view showing the configuration of an API builder unit according to an embodiment of the present invention.

FIG. 5 is a view showing the configuration of an API builder unit according to an embodiment of the present invention.

Referring to FIG. 5, the API builder unit 220 includes a creation module 221, an SQL creation module 222, a test module 223, an analysis module 224, a collection module 225, and a control module 226. The creation module 221 receives patient information and prescription information among the patient information, the medical treatment information, the prescription information, the clinic administration information, and the history information stored in the EMR DB unit 210 and creates a data source. The SQL creation module 222 may create an SQL query and transfer the SQL query to the test module 223 to perform a test. The analysis module 224 may analyze an HTTP request. The collection module 225 may collect query results and create an HPPT response. The control module 226 may control each configuration of the API builder unit 220. That is, the API builder unit may receive data from the EMR DB unit 210 and convert the data into a data of a standardized output format.

Although the present invention has been described with reference to the embodiments shown in the drawings, it is only illustrative, and those skilled in the art may understand that diverse modifications and equivalent other embodiments can be made from the embodiments. Accordingly, the true scope of the present invention should be defined by the spirit of the appended claims.

The invention claimed is:

1. A cloud-based electronic prescription transmission method, wherein a processor and one or more memory devices communicatively coupled to the processor, and the one or more memory devices stores instructions operable when executed by the processor to perform the steps of:
   requesting an electronic prescription from a hospital server, when a cloud server receives a request for the electronic prescription, by the cloud server;
   extracting patient information and prescription information stored in an EMR DB, by the hospital server;
   converting the prescription information according to a unique API; and
   authenticating the converted prescription information through an electronic signature of the clinic, encrypting the converted prescription information, and transmitting the electronic prescription to the cloud server, by the hospital server,
   wherein at the step of converting the prescription information, the prescription information is converted by creating a data source, conveniently creating an SQL query through an SQL query creation guide, converting the data source into a standard data through an API builder, and repeatedly verifying the standard data, wherein the prescription information is converted into standardized prescription information regardless of a heterogeneous database management system (DBMS) of the hospital server, wherein the one or more memory devices stores instructions operable when executed by the processor to further perform the steps of:

constructing an application server;

developing the unique API;

analyzing an HTTP request;

receiving the patient information and the prescription information of the EMR DB to create the data source;

developing a verification process to verify the standard data;

calling an SQL statement;

collecting SQL query results;

creating an HTTP response;

terminating the verification process when a predetermined criterion is satisfied through the verification process; and repeating the verification process when the predetermined criterion is not satisfied.

2. The method according to claim 1, further comprising the steps of:

creating a QR code, and temporarily storing the electronic prescription when a drugstore is selected by the user terminal, by the cloud server; and transmitting at least one among the QR code, the electronic prescription, and drugstore information on the selected drugstore to a drugstore server, by the cloud server.

3. The method according to claim 2, further comprising the steps of:

confirming the electronic prescription, determining whether or not to prepare a medicine, and calculating a medicine price when preparation of the medicine is performed, by the drugstore server; and requesting the cloud server to make a payment, by the drugstore server, and transmitting completion of payment to the drugstore server when making the payment is completed by the user terminal, by the cloud server.

4. The method according to claim 3, further comprising the steps of:

preparing the medicine, and informing the cloud server of completion of preparing the medicine when preparation of the medicine is completed, by the drugstore server, and informing the drugstore server of completion of receiving the medicine, by the cloud server; and storing the electronic prescription by the drugstore server, and deleting the electronic prescription by the cloud server.

5. A cloud-based electronic prescription transmission system comprising:

a processor and one or more memory devices communicatively coupled to the processor;

a cloud server for requesting an electronic prescription from a hospital server when a request for the electronic prescription is received from a user terminal, transmitting at least one among a created QR code, information on a drugstore selected by the user terminal, and the electronic prescription to a drugstore server when the electronic prescription is received from the hospital server, and deleting the electronic prescription when reception of a medicine is informed from the user terminal;

the hospital server for extracting patient information and prescription information from an EMR DB when a request for the electronic prescription is received from the cloud server, converting the prescription information using a unique API, authenticating the converted prescription information through an electronic signature of the clinic, encrypting the prescription information, and transmitting the electronic prescription to the cloud server; and the drugstore server for confirming the electronic prescription when at least one among the QR code, the electronic prescription, and the drugstore information is received from the cloud server, determining whether or not to prepare the medicine, calculating a medicine price, requesting the cloud server to make a payment, and storing the electronic prescription when completion of receiving the medicine is informed, wherein the one or more memory devices stores instructions operable when executed by the processor to perform:

receiving the patient information and the prescription information from the EMR DB and creating a data source;

creating an SQL query and transmitting the SQL query to a test module;

converting the prescription information into standardized prescription information regardless of a heterogeneous database management system (DBMS) of the hospital server;

analyzing an HTTP request;

collecting SQL query results and creating an HTTP response; and controlling each configuration, such that the patient information and the prescription information of the EMR DB is received and the prescription information is converted into the standardized prescription information.

6. The system according to claim 5, wherein the cloud server includes an electronic prescription storage, wherein the electronic prescription storage temporarily stores the electronic prescription when the electronic prescription is received from the hospital server and deletes the stored electronic prescription when reception of the medicine is informed from the user terminal.

7. The system according to claim 5, wherein the drugstore server comprises a processor and one or more memory devices communicatively coupled to the processor, and the one or more memory devices stores instructions operable when executed by the processor to perform:

calculating the medicine price on the basis of the prescription information; and confirming the received electronic prescription and determining whether or not to prepare the medicine.

8. The system according to claim 7, the one or more memory devices stores instructions operable when executed by the processor to further perform:

putting an electronic signature of the clinic on an electronic prescription for drugstore's keeping and storing the electronic prescription in an electronic prescription keeping unit.

* * * * *